United States Patent [19]

Grundei et al.

[11] Patent Number: 4,629,463
[45] Date of Patent: Dec. 16, 1986

[54] CONNECTION OF TUBULAR BONE ENDS

[75] Inventors: Hans Grundei, Lübeck; Thomas Biehl, Munich, both of Fed. Rep. of Germany

[73] Assignee: S & G Implants GmbH, Lubeck, Fed. Rep. of Germany

[21] Appl. No.: 781,256

[22] Filed: Sep. 27, 1985

[30] Foreign Application Priority Data

Sep. 7, 1984 [DE] Fed. Rep. of Germany ....... 3432928

[51] Int. Cl.⁴ .............................. A61F 2/28
[52] U.S. Cl. .................... 623/16; 128/42 YZ
[58] Field of Search ........................... 623/16; 128/924

[56] References Cited

U.S. PATENT DOCUMENTS 2,672,861 12/1952 Jonas .......................... 128/92 YZ
4,016,874 4/1977 Maffei ........................ 128/92 YZ
4,467,794 8/1984 Maffei ........................ 128/92 YZ Primary Examiner—Richard J. Apley
Assistant Examiner—James Prizant
Attorney, Agent, or Firm—Balogh, Osann, Kramer, Dvorak, Genova & Traub

[57] ABSTRACT

The connection of the facing ends of a tubular bone cut by an operation consists of a cylindrical metal pin with an open-cell metallic outer layer on a cylindrical metal core and with annular grooves for receiving stop surfaces which come to bear against the bone ends. The stop surfaces are suitably formed as flat interrupted rings of circumference slightly greater than half the circumference of the annular grooves and arranged to project outwardly of the grooves. A longitudinal groove intersects the annular grooves and receives a longitudinal flange projecting outwardly of the longitudinal groove and connected to the stop surfaces.

The connection may be used as an endoprosthesis in which case only one stop surface is employed.

5 Claims, 6 Drawing Figures

CONNECTION OF TUBULAR BONE ENDS

BACKGROUND OF THE INVENTION

1. Field of the Invention

The invention relates to a connection of the two facing ends of a tubular bone cut by an operation or of a prosthesis part to the end of a tubular bone.

2. Description of the Prior Art

In the treatment of patients, a case can occur where, due to fracture of a bone or due to tumours or the like, a longitudinal part of a tubular bone must be removed by operation and the surgeon must then attempt to reconnect the remaining part lengths to one another and, in doing this, to retain the original bone length. This has hitherto been relatively difficult, and it was sometimes necessary to resort to splinting of the two bone parts.

OBJECTS AND SUMMARY OF THE INVENTION

It is the object of the invention to reconnect the ends of medullary or tubular bones, from which a part length has been removed by operation, to one another in a simple and stable manner while retaining the original bone length.

According to the invention, this object is achieved by a cylindrical metal pin which is provided on the circumference with a longitudinal groove and several annular grooves, of which the annular grooves receive one stop surface or two spaced stop surfaces for the bone end or the facing bone ends and the longitudinal groove receives a longitudinal flange connected to the securing ring and projecting as a surface from the annular groove. Advantageously, the procedure is such that the stop surface or surfaces have the the form of slotted flat securing rings which project outwards from the annular grooves and the circumference of which is slightly greater than half the circumference of the annular grooves.

By means of this solution, the ends of the cylindrical pin can be introduced into the two ends of the medullary bone which has been cut by the operation, a part of the length of the pin, which corresponds to the part of the bone length cut out, remaining free. In this case, stop surfaces are inserted at equal longitudinal spacing into two of the annular grooves, which stop surfaces bear against the facing ends of the cut bone in order to limit the depth of penetration of the pin into the bone cavities, so that the original bone length is restored and maintained. Distortion of the pin is avoided, since the longitudinal flange of the stop surfaces comes into engagement on the one hand in the longitudinal groove of the pin and on the other hand with its outer part into an inner groove to be milled into the bone.

Advantageously, the procedure is such that the stop surface or stop surfaces have the form of slotted flat securing rings which project outwards from the annular grooves and the circumference of which is somewhat greater than half the circumference of the annular grooves, so that these securing rings are pushed over the pin in the region of the grooves and, after expansion, bear against the pin once more. These securing rings can be inserted into corresponding annular grooves, matching the bone length cut out, so that the original bone length is restored and maintained.

BRIEF DESCRIPTION OF THE DRAWINGS

The invention will now be explained by way of example, with reference to the accompanying partly diagrammatic drawings, in which.

DETAILED DESCRIPTION OF THE PREFERRED EMBODIMENT

Figure 1:
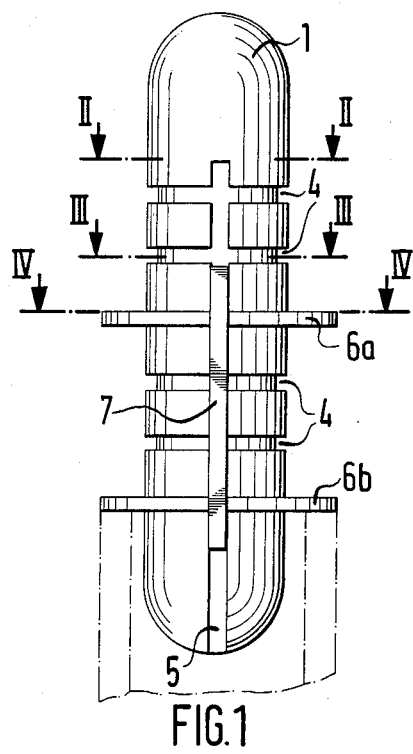
FIG. 1 is a side view of a connecting pin
Figure 2:
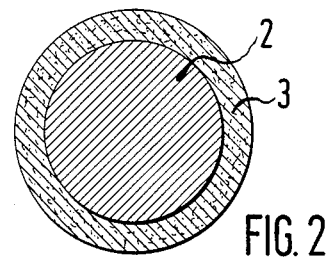
FIGS. 2 and 3 are cross-sections along the lines II—II and III—III respectively of FIG. 1.
Figure 3:
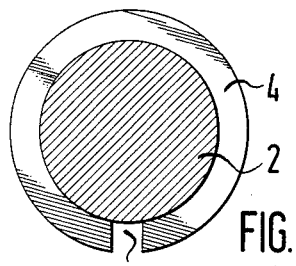

The connecting pin 1 of FIGS. 1 to 4 is a cylindrical metal pin and is advantageously constructed in such a way that a cylindrical metal pin 2 with a smooth outer circumference is provided with a porous or open-cell metal coating 3. The pin 1 is provided, at uniform axial spacings which are as nearly equal as possible, with a number of annular grooves 4, the depth of which suitably corresponds to the thickness of the metal coating 3. In addition, the pin 1 is provided with an outer longitudinal groove 5 which has the same depth as and intersects the grooves 4.

Figure 4:
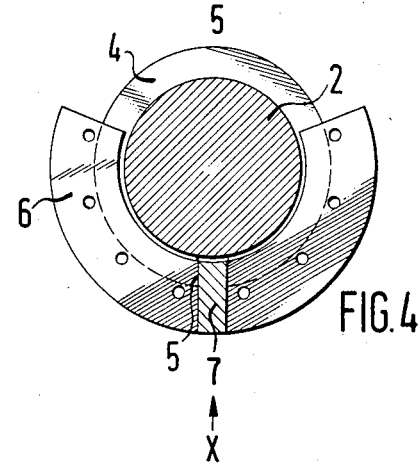
FIG. 4 is a section along line IV—IV of FIG. 1 with a securing ring inserted into an annular groove.

Flat interrupted securing rings 6 are insertable into the annular grooves 4, the internal diameter of the securing rings 6 corresponding to the diameter of the pin 2 and their circumference being slightly greater than half the circumference of the pin 2 as shown in FIG. 4. The flat insertable securing rings 6 project with outer surface parts from the annular grooves 4, as can be seen from FIGS. 1 and 4, and these projecting surface parts form stops for the ends of bones, from which a piece of the length must be operatively removed, for example because of a tumour or other damage. One pin end is then introduced into the medullary cavity at the cut face of the bone until the outer stop length of the securing ring 6a resiliently inserted into an annular groove comes to bear against the cut face of the bone. Correspondingly to the length of the removed piece of bone, a second securing ring 6b is then inserted at a spacing from the securing ring 6a into an annular groove 4, and the adjoining pin end is then inserted or driven into the medullary cavity of the second bone part until the securing ring 6b comes to bear against the cut face of the bone. The connection of the ends of the broken medullary or tubular bone is thus made.

In order to secure the pin 1 against distortion, each securing ring 6 is firmly connected to a longitudinally directed flange 7 which is located perpendicular to the ring and, on insertion of the resilient ring 6, engages in the longitudinal groove 5 and projects outwards for the same distance as the securing ring 6 as shown in FIG. 4. On insertion of the prepared pin 1 into the medullary cavity, the longitudinal flange 7 comes into engagement with a groove milled beforehand in the medullary cavity in the bone. This ensures securing against rotation of the two bone parts relative to one another.

Figure 6:
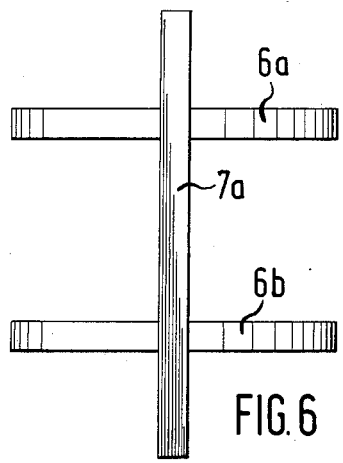
FIG. 6 is a similar view to that of FIG. 5 of two securing rings firmly connected to one another.
Figure 5:
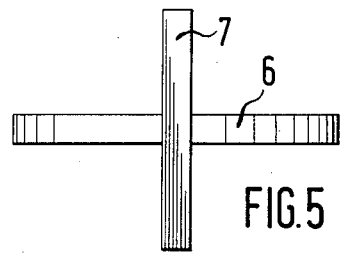
FIG. 5 is a side view of the securing ring, as seen in the direction of the arrow X of FIG. 4.

In place of two separate securing rings 6, two securing rings 6a and 6b can also be firmly connected to one another by a longitudinally directed flange 7a as shown in FIG. 6, it being necessary for the spacing of the two securing rings to be matched to the bone length to be removed and also to the existing ring grooves 4.

As already mentioned, the pin 1 can also be a fixed part of an endoprosthesis, so that it is then only necessary to introduce one pin end into the medullary cavity of a bone up to the stop of a securing ring.

Whilst the invention and many of its attendant advantages will be understood from the foregoing description, it will be apparent that various changes may be made in the form, construction and arrangement of the parts without departing from the spirit and scope of the invention or sacrificing all of its material advantages, the form hereinbefore described merely being a preferred embodiment thereof.

What is claimed is:

1. A connection for the end of a tubular bone which has been cut in an operation said connection comprising a cylindrical metal pin on which is provided comprising a longitudinal groove and several spaced annular grooves, of which at least one annular groove receives a stop surface for the bone end and the longitudinal groove receives a longitudinal flange connected to the stop surface and having a surface projecting from the longitudinal groove.

2. A connection as claimed in claim 1 for the facing ends of a tubular bone cut by an operation in which two spaced stop surfaces are provided, the stop surfaces being disposed in respective annular grooves and connected to the longitudinal flange.

3. A connection as claimed in claim 1, wherein the cylindrical metal pin comprises a cylindrical core with a metallic open-cell coating and the depth of the annular grooves and of the longitudinal groove corresponds to the thickness of the metallic opencell coating.

4. A connection as claimed in claim 1 wherein the at least one stop surface has the form of a flat interrupted securing ring which project outwardly from the annular grooves and the circumference of which is slightly greater than half the circumference of the annular groove.

5. A connection as claimed in claim 2 wherein the longitudinally directed flange is firmly connected at the desired spacing to the two-spaced support surfaces which are formed as securing rings engaging in respective annular grooves.

* * * * *